(12) United States Patent
Wang

(10) Patent No.: US 8,252,215 B2
(45) Date of Patent: Aug. 28, 2012

(54) METHOD FOR FABRICATING A STENT WITH NUCLEATING AGENT

(75) Inventor: Yunbing Wang, Sunnyvale, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 866 days.

(21) Appl. No.: 12/059,423

(22) Filed: Mar. 31, 2008

(65) Prior Publication Data

US 2009/0248147 A1    Oct. 1, 2009

(51) Int. Cl.
  *B29C 47/00* (2006.01)
  *B29D 22/00* (2006.01)
  *A61F 2/06* (2006.01)

(52) U.S. Cl. ........ 264/150; 264/151; 264/154; 264/156; 264/209.4; 264/209.5; 264/210.1; 264/210.7; 264/211; 264/211.12; 264/400; 264/523; 264/531; 264/532; 264/540; 264/573; 623/1.15; 623/1.38; 623/1.49

(58) Field of Classification Search .................. None
See application file for complete search history.

(56) References Cited

U.S. PATENT DOCUMENTS

| | | | |
|---|---|---|---|
| 5,997,568 A * | 12/1999 | Liu | 606/228 |
| 6,319,576 B1 | 11/2001 | Rule et al. | |
| 6,669,721 B1 * | 12/2003 | Bose et al. | 623/1.15 |
| 6,932,930 B2 * | 8/2005 | DeSimone et al. | 264/235 |
| 2003/0083732 A1 | 5/2003 | Stinson | |
| 2005/0161859 A1 * | 7/2005 | Miller et al. | 264/209.1 |
| 2006/0020330 A1 | 1/2006 | Huang et al. | |
| 2006/0076708 A1 * | 4/2006 | Huang et al. | 264/239 |
| 2007/0149640 A1 * | 6/2007 | Andjelic et al. | 523/105 |
| 2007/0179253 A1 * | 8/2007 | Matsuoka et al. | 525/438 |
| 2007/0202146 A1 * | 8/2007 | Burgermeister et al. | 424/423 |
| 2007/0231365 A1 | 10/2007 | Wang et al. | |
| 2007/0253999 A1 | 11/2007 | Huang et al. | |
| 2007/0293938 A1 | 12/2007 | Gale et al. | |
| 2008/0177374 A1 * | 7/2008 | Zheng et al. | 623/1.15 |
| 2008/0262150 A1 * | 10/2008 | Takenaka et al. | 524/599 |
| 2009/0204116 A1 * | 8/2009 | Shalaby et al. | 606/62 |

FOREIGN PATENT DOCUMENTS

EP    1 825 870    8/2007

OTHER PUBLICATIONS

International Search Report for PCT/US2009/036291, mailed May 27, 2010, 5 pgs.
U.S. Appl. No. 10/881,554, filed Jun. 29, 2004, Abbate et al.
U.S. Appl. No. 10/956,910, filed Sep. 30, 2004, Huang et al.
U.S. Appl. No. 10/956,911, filed Sep. 30, 2004, Durcan.
U.S. Appl. No. 10/956,759, filed Sep. 30, 2004, Durcan.
Anderson et al., "Melt preparation and nucleation efficiency of polylactide stereocomplex crystallites", Polymer, vol. 47, pp. 2030-2035 (2006).
Brizzolara et al., "Mechanism of the Stereocomplex Formation between Enantiomeric Poly(lactide)s", Macromolecules, vol. 29, pp. 191-197 (1996).
Krouse et al., "Stereocomplex Formation between Enantiomeric Poly(lactides)", Macromolecules, vol. 20, pp. 904-906 (1987).

(Continued)

*Primary Examiner* — Jeffrey Wollschlager
(74) *Attorney, Agent, or Firm* — Squire Sanders (US) LLP

(57) ABSTRACT

The use of nucleating agents to manufacture polymeric stents is disclosed. The resulting stents may have increased crystallinity, decreased crystal size, increased mechanical properties, and faster degradation times.

10 Claims, 5 Drawing Sheets

OTHER PUBLICATIONS

Sarasua et al., "Crystallization and Melting Behavior of Polylactides", Macromolecules 31, pp. 3895-3905 (1998).

Schmidt et al., "Polylactide Stereocomplex Crystallites as Nucleating Agents for Isotactic Polylactide", Journal of Polymer Science: Part B: Polymer Physics, vol. 39, pp. 300-313 (2001).

Reeve et al., "Polylactide Stereochemistry: Effect on Enzymatic Degradability", Macromolecules 27, pp. 825-831 (1994).

Takasaki et al., "Development of Stereocomplex Crystal of Polylactide in High-Speed Melt Spinning and Subsequent Drawing and Annealing Processes", Journal of Macromolecular Science: Part B—Physics, vol. B42, Nos. 3 & 4, pp. 403-420 (2003).

Tsuji et al., "Stereocomplex Formation between Enantiomeric Poly(lactic acid)s. 2. Stereocomplex Formation in Concentrated Solutions", Macromolecules, vol. 24, pp. 2719-2724 (1991).

Tsuji et al., "Stereocomplex Formation between Enantiomeric Poly(lactic acid)s. 9. Stereocomplexation from the Melt", Macromolecules, vol. 26, pp. 6918-6926 (1993).

Urayama et al., "Controlled crystal nucleation in the melt-crystallization of poly(L-lactide) and poly(L-lactide)/poly(D-lactide) stereocomplex", Polymer, vol. 44, pp. 5635-5641 (2003).

Van Vlack, "Elements of Materials Science and Engineering", $6^{th}$ ed., 4 pages (1989).

Yash Khanna, "Rheological Mechanism and Overview of Nucleated Crystallization Kinetics", macromolecules, vol. 26, pp. 3639-3643 (1993).

White et al., "Specification of Biaxial Orientation in Amorphous and Crystalline Polymers", Pol. Engineering and Science vol. 21, No. 13, pp. 859-868 (1981).

* cited by examiner

METHOD FOR FABRICATING A STENT WITH NUCLEATING AGENT

BACKGROUND OF THE INVENTION

1. Field of the Invention

This invention relates to methods of using nucleating agents in stent manufacturing.

2. Description of the State of the Art

This invention relates to radially expandable endoprostheses, which are adapted to be implanted in a bodily lumen. An "endoprosthesis" corresponds to an artificial device that is placed inside the body. A "lumen" refers to a cavity of a tubular organ such as a blood vessel.

A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a retractable sheath or a sock. When the stent is in a desired bodily location, the sheath may be withdrawn which allows the stent to self-expand.

The stent must be able to satisfy a number of mechanical requirements. First, the stent must be capable of withstanding the structural loads, namely radial compressive forces, imposed on the stent as it supports the walls of a vessel. Therefore, a stent must possess adequate radial strength. Radial strength, which is the ability of a stent to resist radial compressive forces, is due to strength and rigidity around a circumferential direction of the stent. Radial strength and rigidity, therefore, may also be described as, hoop or circumferential strength and rigidity.

Once expanded, the stent must adequately maintain its size and shape throughout its service life despite the various forces that may come to bear on it, including the cyclic loading induced by the beating heart. For example, a radially directed force may tend to cause a stent to recoil inward. Generally, it is desirable to minimize recoil.

In addition, the stent must possess sufficient flexibility to allow for crimping, expansion, and cyclic loading. Longitudinal flexibility is important to allow the stent to be maneuvered through a tortuous vascular path and to enable it to conform to a deployment site that may not be linear or may be subject to flexure. Finally, the stent must be biocompatible so as not to trigger any adverse vascular responses.

The structure of a stent is typically composed of scaffolding that includes a pattern or network of interconnecting structural elements often referred to in the art as struts or bar arms. The scaffolding can be formed from wires, tubes, fibers, or sheets of material rolled into a cylindrical shape. The scaffolding is designed so that the stent can be radially compressed (to allow crimping) and radially expanded (to allow deployment). A conventional stent is allowed to expand and contract through movement of individual structural elements of a pattern with respect to each other.

Additionally, a medicated stent may be fabricated by coating the surface of either a metallic or polymeric scaffolding with a polymeric carrier that includes an active or bioactive agent or drug. Polymeric scaffolding may also serve as a carrier of an active agent or drug.

Furthermore, it may be desirable for a stent to be biodegradable. In many treatment applications, the presence of a stent in a body may be necessary for a limited period of time until its intended function of, for example, maintaining vascular patency and/or drug delivery is accomplished. Therefore, stents fabricated from biodegradable, bioabsorbable, and/or bioerodable materials such as bioabsorbable polymers should be configured to completely erode only after the clinical need for them has ended.

There are several characteristics that are important for implantable medical devices, such as stents, including high radial strength and good fracture toughness. Some crystalline or semi-crystalline polymers that may be suitable for use in implantable medical devices have potential shortcomings with respect to some of these characteristics, in particular, fracture toughness.

Current polylactide or poly(lactic acid) (PLA) stents have slow degradation times (about 3 years or more). Substitutions such as the use of poly(glycolide-co-lactide) or poly(glycolic acid-co-lactic acid) (PLGA) materials have been made in the past to shorten the degradation rate. However, this resulted in deteriorated mechanical properties and stability of the formed stent due to low crystallinity and low crystallization rate. Thus, there is a need for a faster degrading PLGA stent without sacrificing mechanical properties or stability.

SUMMARY OF THE INVENTION

Several embodiments of the present invention are directed to a method of fabricating a polymeric stent including combining a polymer such as PLGA with a nucleating agent to form a polymer mixture, forming polymer tubing from the polymer mixture, and fabricating the stent from the tubing. The nucleating agent is used to increase the crystallinity and decrease the crystal size of the polymer tubing.

In certain embodiments, the nucleating agent includes polyglycolide (PGA), poly(glycolide-co-lactide) (PGLA) with small amount or lactide (less than 10%), inorganic compounds, or organic compounds.

Some embodiments are directed to a method of fabricating a polymeric stent including combining PLGA with a nucleating agent to form a polymer mixture, forming polymer tubing from the polymer mixture, stress inducing crystallization, and fabricating the stent from the tubing. The nucleating agent and the stress inducing step increase the crystallinity of the polymer tubing as the tubing is extruded and during the stress inducing step. The blending of the polymer and the nucleating agent may be accomplished using mechanical blending, melt blending, solution blending, or combinations thereof.

In an embodiment, the tubing extrusion step is immediately followed by a deformation step. In other embodiments, after the tubing has been extruded, the tubing is cooled and then reheated for the stress inducing step.

In several embodiments, the stress inducing crystallization step includes deformation of the polymer tubing radially, axially, or both. In some embodiments, blow molding is used to deform the polymer tubing.

Some embodiments of the invention are directed to a polymeric stent comprising PLGA with PGA added as a nucleating agent.

Other embodiments are directed to a polymeric stent where PLGA and a nucleating agent are blended together, wherein the nucleating agent is an inorganic or organic compound.

DETAILED DESCRIPTION OF THE INVENTION

Figure 1:
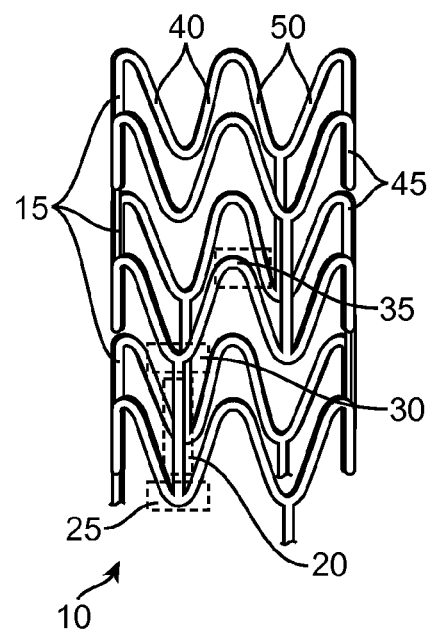
FIG. 1 depicts a stent.

The various embodiments of the present invention relate to a polymer stent composition and methods of fabricating a polymeric stent that have good or optimal toughness and selected mechanical properties along the axial direction or circumferential direction of the stent, or both. The present invention can be applied to devices including, but is not limited to, self-expandable stents, and balloon-expandable stents.

For the purposes of the present invention, the following terms and definitions apply:

The "glass transition temperature," $T_g$, is the temperature at which the amorphous domains of a polymer change from a brittle, vitreous state to a solid, deformable or ductile state at atmospheric pressure. In other words, the $T_g$ corresponds to the temperature where the onset of segmental motion in the chains of the polymer occurs. When an amorphous or semi-crystalline polymer is exposed to an increasing temperature, the coefficient of expansion and the heat capacity of the polymer both increase as the temperature is raised, indicating increased molecular motion. As the temperature is raised the actual molecular volume in the sample remains constant, and so a higher coefficient of expansion points to an increase in free volume associated with the system and therefore increased freedom for the molecules to move. The increasing heat capacity corresponds to an increase in heat dissipation through movement. $T_g$ of a given polymer can be dependent on the heating rate and can be influenced by the thermal history of the polymer. Furthermore, the chemical structure of the polymer heavily influences the glass transition by affecting mobility.

"Stress" refers to force per unit area, as in the force acting through a small area within a plane. Stress can be divided into components, normal and parallel to the plane, called normal stress and shear stress, respectively. Tensile stress, for example, is a normal component of stress applied that leads to expansion (increase in length). In addition, compressive stress is a normal component of stress applied to materials resulting in their compaction (decrease in length). Stress may result in deformation of a material, which refers to a change in length. "Expansion" or "compression" may be defined as the increase or decrease in length of a sample of material when the sample is subjected to stress.

"Strain" refers to the amount of expansion or compression that occurs in a material at a given stress or load. Strain may be expressed as a fraction or percentage of the original length, i.e., the change in length divided by the original length. Strain, therefore, is positive for expansion and negative for compression.

"Modulus" may be defined as the ratio of a component of stress or force per unit area applied to a material divided by the strain along an axis of applied force that results from the applied force. For example, a material has both a tensile and a compressive modulus.

"Solvent" is defined as a substance capable of dissolving or dispersing one or more other substances or capable of at least partially dissolving or dispersing the substance(s) to form a uniformly dispersed mixture at the molecular- or ionic-size level. The solvent should be capable of dissolving at least 0.1 mg of the polymer in 1 ml of the solvent, and more narrowly 0.5 mg in 1 ml at ambient temperature and ambient pressure.

"Non-solvent" is defined as a substance incapable of dissolving the other substance. The non-solvent should be capable of dissolving only less than 0.1 mg of the polymer in 1 ml of the non-solvent at ambient temperature and ambient pressure, and more narrowly only less than 0.05 mg in 1 ml at ambient temperature and ambient pressure.

"Percent crystallinity" refers to the percentage of the polymer material that is in a crystalline form. It is thought that the methods of the present invention can increase the percent crystallinity of the polymer.

Those of ordinary skill in the art understand that there are several methods for determining the percent crystallinity in polymers. These methods are, for example, described in L. H. Sperline, Introduction to Physical Polymer Science (3rd ed. 2001). The first involves the determination of the heat of fusion of the whole sample by calorimetric methods. The heat of fusion per mole of crystalline material can then be estimated independently by melting point depression experiments. The percent crystallinity is then given by heat of fusion of the whole sample divided by the heat of fusion per mole of crystalline material times 100. Representative example of this process and calculation are described in Sarasua et al., Crystallization and Melting Behavior of Polylactides, Macromolecules 31(12), 3895-3905 (1998); and Reeve et al., Polylactide Stereochemistry: Effect of Enzymatic Degradability, Macromolecules 27(3), 825-31 (1994) (citing Bloembergen et al., Studies of Composition and Crystallinity of Bacterial Poly(β-hydroxybutyrate-co-β-hydroxyvalerate, Macromolecules 19(11), 2865-70 (1986)).

A second method stems from the fact that X-ray diffraction depends on the number of electrons involved and is thus proportional to the density. Besides Bragg diffraction lines for the crystalline portion, there is an amorphous halo caused by the amorphous portion of the polymer. The amorphous halo occurs at a slightly smaller angle than the corresponding crystalline peak, because the atomic spacings are larger. The amorphous halo is broader than the corresponding crystalline peak, because of the molecular disorder. This second method can be quantified by the crystallinity index, CI, where $$CI = \frac{Ac}{Aa + Ac}$$

and where Ac and Aa represent the area under the Bragg diffraction line and corresponding amorphous halo, respectively.

A stent may include a pattern or network of interconnecting structural elements or struts. FIG. 1 depicts an example of a three-dimensional view of a stent 10. The stent may have a pattern that includes a number of interconnecting elements or struts 15. The embodiments disclosed herein are not limited to stents or to the stent pattern illustrated in FIG. 1. The structural pattern of the device can be of virtually any design, The variations in the structure of patterns are virtually unlimited. As shown in FIG. 1 the geometry or shape of stents vary throughout its structure. A pattern may include portions of struts that are straight or relatively straight, an example being a section 20. Patterns may also include intersections of struts with curved or bent portions or elements as in sections 25 and 30. In addition, patterns may include struts that include curved or bent portions or elements as in a section 35.

Additionally, a surface of a medical device, such as a stent, may also be characterized by the relative location of the surface with respect to a bodily lumen. The stent includes abluminal surfaces or outer portions, luminal surfaces or inner portions, and surfaces between the abluminal and luminal surfaces. For example, struts 15 of stent 10 include luminal faces or surfaces 40, abluminal faces or surfaces 45, and side-wall faces or surfaces 50.

A stent such as stent 10 may be fabricated from a polymeric tube or a sheet by rolling and bonding the sheet to form the tube. A tube or sheet can be formed by extrusion or injection molding. A stent pattern, such as the one pictured in FIG. 1, can be formed in a tube or sheet with a technique such as laser cutting or chemical etching. Representative examples of lasers that may be used include, but are not limited to, excimer, carbon dioxide, and YAG. The stent can then be crimped on to a balloon or catheter for delivery into a bodily lumen.

The underlying structure or substrate of a stent can be completely or at least in part made from a biodegradable polymer or combination of biodegradable polymers, a biostable polymer or combination of biostable polymers, or a combination of biodegradable and biostable polymers. Additionally, a polymer-based coating for a surface of a device can be a biodegradable polymer or combination of biodegradable polymers, a biostable polymer or combination of biostable polymers, or a combination of biodegradable and biostable polymers.

There are several mechanical properties that are important for a stent. These include high radial strength, adequate toughness, low recoil, and resistance to physical aging. A stent must have adequate strength, particularly, in the radial direction to withstand structural loads, namely radial compressive forces, imposed on the stent as it supports the walls of a vessel. Radial strength is associated with strength of the stent around the circumferential direction of the stent. In addition, the stent must possess sufficient toughness so that the stent exhibits sufficient flexibility to allow for crimping, expansion, and flexure. A stent should have sufficient toughness so that it is resistant to crack formation, particularly, in high strain regions. Recoil refers to the retraction of a stent radially inward from its deployed diameter.

A stent can be made in whole or in part of a biodegradable polymer. A biodegradable stent can be configured to erode from an implant site when it is no longer needed. A biodegradable stent allows further surgery or intervention, if necessary, on a treated vessel and reduces the likelihood of late stent thrombosis, a condition in which clots form on the surface of the stent months or years after deployment. Some crystalline or semi-crystalline biodegradable polymers that are glassy or have a glass transition temperature (Tg) above body temperature are particularly attractive as stent materials due to their strength and stiffness at physiological conditions. Such glassy polymers can be absorbed through chemical degradation, such as hydrolysis. Physiological conditions refer to conditions that an implant is exposed to within a human body. Physiological conditions include, but are limited to, human body temperature, approximately 37° C.

However, the mechanical properties of such polymers may require improvement to be suitable as stent materials. For example, the struts of stent may have to be undesirably large to have radial strength sufficient to support the walls of a vessel. Therefore, the strength of such polymers may need improvement. Additionally, the toughness of such polymers can be lower than desired, in particular, for use in stent applications. For example, polymers such as poly(L-lactide) (PLLA) are stiff and strong, but tend to be brittle under physiological conditions. These polymers can exhibit a brittle fracture mechanism at physiological conditions in which there is little or no plastic deformation prior to failure. A stent fabricated from such polymers can have insufficient toughness for the range of use of a stent. As a result, cracks, particularly in high strain regions, can be induced, which can result in mechanical failure of the stent.

Furthermore, recoil can result from creep and stress relaxation which result from relaxation or rearrangement of polymer chains. Creep refers to the gradual deformation that occurs in a polymeric construct subjected to an applied load. Stress relaxation occurs when deformation (or strain) is constant and is manifested by a reduction in the force (stress) required to maintain a constant deformation Physical aging can also be a problem with such semicrystalline polymers. Physical aging, as used herein, refers to densification in the amorphous regions of a semi-crystalline polymer. Densification is the increase in density of a material or region of a material and results from reordering of polymer chains. Densification tends to decrease the fracture toughness of a polymer.

In general, the mechanical properties of a polymer depend upon its morphology or microstructure. Various embodiments of the present invention include processing a polymeric construct that is a precursor to a stent to obtain desirable or selected mechanical properties of the stent. Such desirable or selected mechanical properties can correspond to a particular structure or morphology. Embodiments of the present invention include adjusting the processing conditions to obtain selected or desirable properties.

Morphology includes crystallinity, molecular orientation of polymer chains, and crystal size. A polymer may be completely amorphous, partially crystalline, or almost completely crystalline. A partially crystalline polymer includes crystalline regions separated by amorphous regions. The degree of crystallinity is the sum of all the crystalline regions. Molecular orientation refers to the relative orientation of polymer chains along a longitudinal or covalent axis of the polymer chains. The orientation can refer to both the orientation of polymer chains the crystalline regions and the amorphous regions.

The relationship between the morphology and mechanical properties can be of use in alleviating some of the shortcomings of the semi-crystalline polymers mentioned above. In general, the modulus of a polymer increases as crystallinity increases. As mentioned above, a semi-crystalline polymer with a high degree of crystallinity can be brittle and is susceptible to cracking. An amorphous polymer may be more flexible or ductile, but may have insufficient radial strength. Additionally, the size of crystalline regions in a polymer can affect mechanical properties. It is believed that decreasing the size of crystalline regions or domains while maintaining a degree of crystallinity in a polymer increases the fracture toughness of the polymer.

Figure 2A:
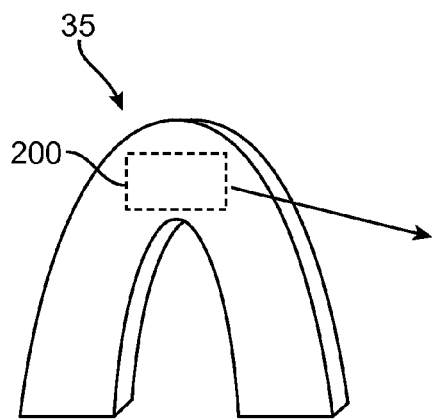
FIGS. 2A, B depict a portion of the stent in FIG. 1 without a nucleating agent.
Figure 2B:
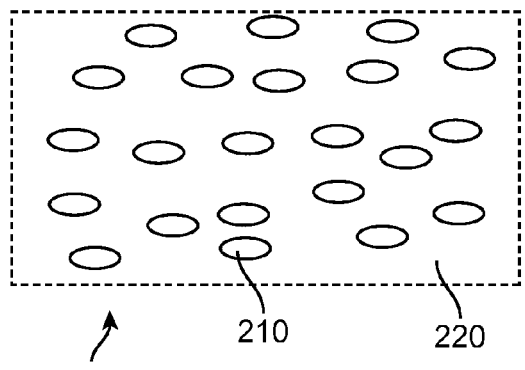

FIGS. 2A, B depict a blown up view of a portion 35 of a strut 10 (shown in FIG. 1) with area 200 that has been deformed without the use of a nucleating agent. The crystalline domains 210 dispersed in amorphous domain 220 are less numerous as compared to FIG. 3B, where portion 300 has a greater number of smaller crystalline domains 310 dispersed in amorphous domain 320.

Figure 3A:
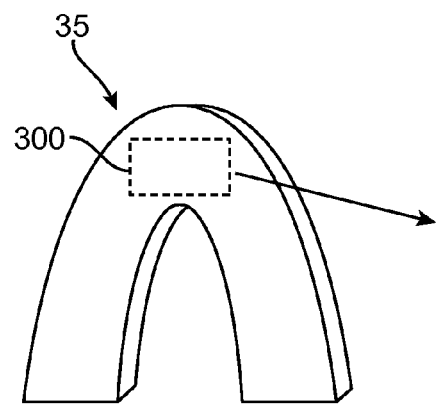
FIGS. 3A, B depict a portion of the stent in FIG. 1 including a nucleating agent.
Figure 3B:
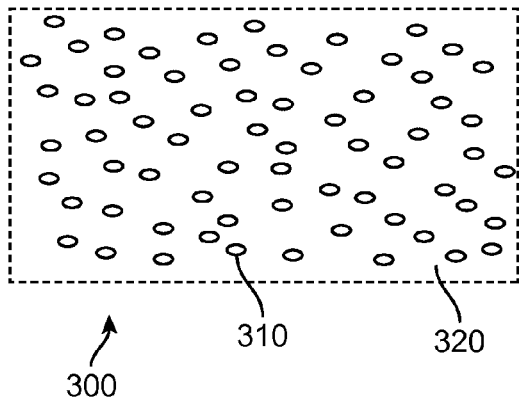

FIGS. 3A, B depict a blown up view of a portion of 35 of strut 10 with area 300 that has been deformed where the polymer has been blended with a nucleating agent. The crystalline domains 310 are more numerous, and are smaller in size. The size of the crystals is also smaller.

Small crystalline domains 310 serve as net-points to constrain polymer chains in the amorphous domain 320 of portion 300. The motion of the polymer chains is restricted through the high number of small crystalline domains 310.

Figure 4:
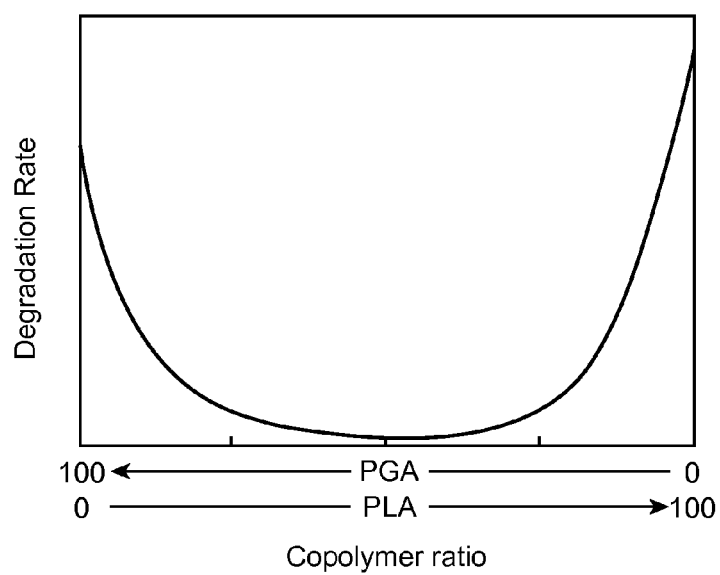
FIG. 4 depicts the degradation rates of a PGA and PLA polymers.

As mentioned above, current PLLA stents have degradation times of about 3 years or more. Poly(lactide-co-glycolide) (PLGA) polymeric material with less than about 25 wt % glycolide (GA) may be used to replace PLLA as a stent polymer material to accelerate the degradation rate. In some embodiments, the wt % of GA is from 5 wt % to 15 wt %. However, PLGA has a slow crystallization rate and low crystallinity. For PLGA, the GA content may be manipulated to change the degradation time. FIG. 4 graphically shows how the degradation rate changes with the amount of GA in the polymer. If the GA content is increased from about 5 wt % to about 15 wt %, then the degradation time is expected to change from about 28 months to about 18 months. However, as the GA content in the PLGA increases, the crystallization rate and crystallinity of the resulting polymer decrease, which would deteriorate the mechanical properties and stability of a formed stent.

The embodiments below use PLGA for the polymer portion of the polymer/nucleating agent blend. However, other useful polymers for the polymer portion are PLA, poly(lactide-co-caprolactone)(PLA-PCL), poly(lactide-co-trimethylene carbonate)(PLA-PTMC), and poly(lactide-co-p-dioxanone)(PLA-PDO).

In several embodiments of the present invention, the crystallinity and crystallization rate of a PLGA polymer may be increased by adding a nucleating agent. The nucleating agent can be a fast crystallizing polymer, or a crystallizing organic or inorganic compound. To form the polymer/nucleating agent mixture, mechanical blending, melt blending, solution blending, or combinations thereof may be used. Mechanical blending may be accomplished by using a mechanical blender. A twin screw extruder may be used for melt blending. Solution blending may be accomplished by dissolving both the polymer and nucleating agent in a co-solvent and then precipitating them in a non-solvent.

In one embodiment, the polymeric nucleating agent is polyglycolide or poly(glycolic acid) (PGA) and is combined with PLGA. In certain embodiments, PGA and PLGA are combined using melt extrusion. In several embodiments the amount of nucleating agent is about 0.1 to about 10% by weight. In certain embodiments, the amount of nucleating agent is about 0.2 to about 5% by weight. PGA would form a small crystalline structure first, and these small crystals would increase nucleation density and accelerate the entire crystallization rate of the PLGA matrix material. PGA alone has a fast degradation rate (typically less than one year to degrade), and its degradation product and micro-pore structure created by the degradation of PGA would accelerate the degradation of the PLGA matrix. Upon manufacturing a stent using the nucleated matrix, the stent would posses both improved mechanical properties and a faster degradation rate.

In an embodiment, for the PLGA, the LLA:GA ratio is in the range of about 80:20 to 99.99:0.01, or about 85:15 to about 95:5. As the GA content increases in the PLGA, then the crystallization rate and crystallinity may decrease, which leads to reduced stability. In certain embodiments, the nucleating agent is 0.1 to 10 wt %, 0.2 to 5 wt %, or 5 wt % PGA and is blended with PLGA (LLA:GA=90:10) to form a polymer mixture with increased crystallinity or decreased crystal size.

In another embodiment, the polymeric nucleating agent is poly(lactide-co-glycolide) (PGLA) with less than about 10 wt % L-lactide, and the PGLA is combined with PLGA. In certain embodiments the amount of nucleating agent is about 0.1 to about 10% by weight. In some embodiments, the amount of nucleating agent is about 0.2 to about 5% by weight. PGLA has a faster crystallization rate than the PLGA and also a faster degradation rate than the PGA mentioned above. When PGLA is used instead of PGA as a nucleating agent, a PLGA stent containing the PGLA nucleating agent would possess an even faster degradation rate than a stent using PGA as a nucleating agent.

In an embodiment, in the PLGA, the LLA:GA ratio is about 80:20 to about 99.99:0.01, or about 85:15 to about 95:5. For the nucleating agent, PGLA can be used where the GA:LLA ratio is about 90:10 to about 99.99:0.01, or about 95:5 to about 99:1. In certain embodiments, the nucleating agent is 5 wt % PGLA (GA:LLA=98:2) and is blended with PLGA (LLA:GA=90:10) to form a polymer mixture with increased crystallinity.

In several embodiments, the nucleating agent is an organic or inorganic compound. Organic or inorganic nucleating agents may include, but are not limited to, nano Mg silicate hydrate, ethylene bis (1,2-hydroxystearylamide), boron nitride, hydroxyapatite, decamethylenedicarboxylichydrazide, dibenzoylhydrazide, dioctyl phthalate, citric acid esters, lactic acid esters, lactide esters, ethyl lactate, triphenyl phosphate, glycerine, acetin, and butyrin. In certain embodiments the amount of nucleating agent is about 0.1 to about 10% by weight. In some embodiments, the amount of nucleating agent is about 0.2 to about 5% by weight. With respect to organic or inorganic compounds, nano particles may provide improved radial strength and toughness. Any of the above listed compounds can be in the form of nano particles, for example Mg silicate hydrate with a size of 10 nm to 500 nm.

In an embodiment using the organic or inorganic nucleating agents above, for the PLGA, the LLA:GA ratio is in the range of about 80:20 to about 99.99:0.01, or about 85:15 to about 95:5. In certain embodiments, the nucleating agent is 1 wt % nano magnesium silicate hydrate and is blended with PLGA (LLA:GA ratio=90:10) to form a polymer mixture with increased crystallinity and decreased crystal size.

For the blending of the PLGA with a nucleating agent, conventional melt compounding into a PLGA matrix using melt compounding equipment may be used. Examples of melt compounding equipment includes, but is not limited to, single and twin screw extruders, roll mills, Banbury mixers, and Farrell continuous mixers. In certain embodiments, the nucleating agent may be added during the PLGA tubing extrusion process through a separate feeding window.

A further embodiment of combining the PLGA and the nucleating agent is through solution blending. PLGA and the nucleating agent are both dissolved in a co-solvent and then precipitated in a non-solvent. The resulting mixture may then be used to form tubing using one of the extrusion methods mentioned above. Examples of co-solvents include, but are not limited to, chloroform, ethylene dichloride, tetrahydrofuran (THF), and combinations thereof. Examples of non-solvents include, but are not limited to, methanol, ethanol, isopropanol, pentane, hexane, and combinations thereof.

The PLGA/nucleating agent compositions discussed above may be used in the manufacturing/deforming procedures discussed below.

The strength and toughness of the polymer including the nucleating agent can be affected by the orientation of polymer chains. The toughness of a semi-crystalline polymer can be increased by inducing orientation of polymer chains in both the crystalline and amorphous regions. In addition, the strength of the polymer is also increased along the direction of preferred orientation.

It is believed that crystalline domains can act as net points to tie polymer chains in the amorphous regions between the domains. Smaller domains at a given degree of crystallinity result in a greater number of domains and tie molecules, resulting in increased toughness. The strength and toughness of the amorphous regions can be further be increased by inducing orientation in the amorphous regions. It is expected that a higher number of net points and tie molecules with induced orientation can lead to higher strength and fracture toughness.

Certain embodiments of the present invention include processing a stent precursor construct, such as a polymer tube with the polymeric material including a nucleating agent, to modify the morphology of the polymer in the construct so that the construct has desired or selected properties. It is well known by those skilled in the art that the mechanical properties of a polymer can be modified by applying stress to a polymer. James L. White and Joseph E. Spruiell, Polymer and Engineering Science, 1981, Vol. 21, No. 13. The application of stress can induce molecular orientation along the direction of stress which can modify mechanical properties along the direction of applied stress. Induced orientation in constructs such as polymer tubes can be particularly useful since tubes formed by extrusion tend to possess no or substantially no polymer chain alignment in the circumferential direction. A tube made from injection molding has a relatively low degree of polymer chain alignment in both the axial and circumferential directions.

Molecular orientation can be induced in polymers that are completely amorphous, partially or semi-crystalline, or almost completely crystalline. A partially or semi-crystalline polymer includes crystalline regions separated by amorphous regions. The crystalline regions do not necessarily have the same or similar orientation of polymer chains. However, a high degree of orientation of crystallites may be induced by applying stress to a semi-crystalline polymer. The stress may also induce orientation in the amorphous regions.

Due to the magnitude and directions of stresses imposed on a stent during use, it is important for the mechanical stability of a device to have an adequate magnitude of strength both in axial and circumferential directions. Therefore, an adequate balance of axial and circumferential strength is also important for mechanical stability. The relative amount of axial and circumferential orientation may depend on a number of factors such as the stent pattern, initial diameter of the tube, final diameter of the stent, and crimped diameter of the stent. Polymer tubes formed by extrusion methods, such as those with polymeric materials including nucleating agents, tend to possess a significant degree of axial polymer chain alignment. However, such conventionally extruded tubes tend to possess no or substantially no polymer chain alignment in the circumferential direction.

Some embodiments of a method of fabricating a stent may include radially deforming a polymeric tube about a cylindrical axis of the tube, wherein the polymeric material contains a nucleating agent. The tube can be radially deformed to increase the strength and modulus in the circumferential direction. The increase in strength and modulus can be due to the induced molecular orientation in the circumferential direction.

Additionally, the method may further include axially deforming the polymeric tube along the cylindrical axis of the tube. In one embodiment, the tube may be axially deformed by applying a tensile force to the tube along the cylindrical axis. Axial deformation of the polymer tube may induce axial molecular orientation, and hence, increase the axial strength and modulus or rigidity. Various embodiments may include radially deforming the tube prior to, subsequent to, and/or contemporaneously with axial deformation the tube.

The degree of polymer chain alignment induced with applied stress may depend upon the temperature of the polymer. Above Tg, polymer chain alignment may be readily induced with applied stress since polymer chains have greater mobility than below Tg. Consequently, the amount of deformation depends on the temperature of a polymeric material. Therefore, it is advantageous to radially deform the tube at a temperature above Tg.

Additionally, the polymeric tube including a nucleating agent may be heat set to allow polymeric chains to rearrange upon deformation. "Heat setting," as used herein, refers to maintaining a polymer at an elevated temperature to allow polymer chains in the heated polymer to move toward a state of thermodynamic equilibrium. In a deformed polymeric tube where the polymeric material includes a nucleating agent, polymeric chains are allowed to equilibrate towards the induced highly oriented structure at the elevated temperature. Since polymer chain alignment is a time and temperature dependent process, a highly oriented structure that is thermodynamically stable at a given temperature may not be formed instantaneously. Thus, the polymeric tube may be maintained in a deformed state at an elevated temperature for a period of time.

Figure 5:
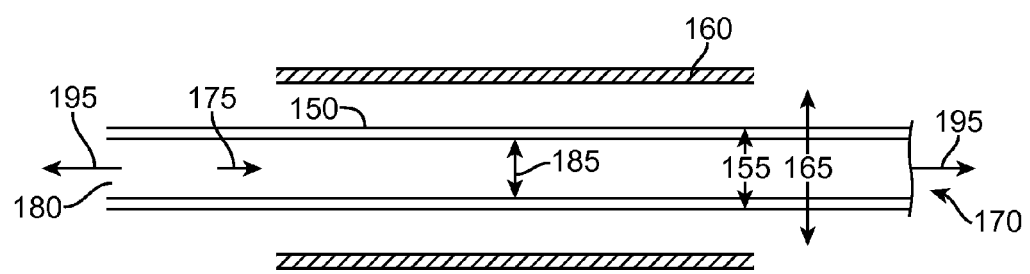
FIG. 5 depicts an axial cross-section of a polymer tube positioned within an annular member or mold.
Figure 6:
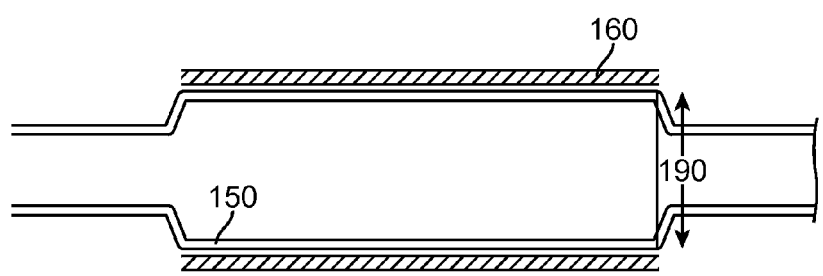
FIG. 6 depicts a deformed polymeric tube in a mold.

A tube made of a polymeric material including a nucleating agent can be radially deformed using blow molding. FIGS. 5 and 6 illustrate an embodiment of deforming a polymeric tube in manufacturing a stent. FIG. 5 depicts an axial cross-section of a polymeric tube 150 with an outside diameter 155 positioned within an annular member or mold 160. Mold 160 may act to limit the radial deformation of polymeric tube 150 to a diameter 165, the inside diameter of mold 160. Polymer tube 150 may be closed at a distal end 170. Distal end 170 may be open in subsequent manufacturing steps. A fluid may be conveyed, as indicated by an arrow 175, into an open proximal end 180 of polymeric tube 150. A tensile force 195 is applied at proximal end 180 and a distal end 170.

Polymeric tube 150 may be heated by heating the gas to a temperature above ambient temperature prior to conveying the gas into polymeric tube 150. Alternatively, the polymeric tube may be heated by heating the exterior of mold 160. The tube may also be heated by the mold. The increase in pressure inside of polymer tube 150 facilitated by an increase in temperature of the polymeric tube causes radial deformation of polymer tube 150, as indicated by an arrow 185. FIG. 6 depicts polymeric tube 150 in a deformed state with an outside diameter 190 within annular member 160.

Additionally, as indicated above, the pressure inside the tube and the temperature of the tube may be maintained at the elevated temperature for a period of time to allow the polymeric tube to be heat set. The period of time may be between about one minute and about two hours, or more narrowly, between about two minutes and about ten minutes.

Furthermore, the tube may be expanded to a target diameter. In one embodiment, the target diameter may be the diameter at which a stent pattern is formed by laser machining the tube. The target diameter can also correspond to the diameter of a stent prior to crimping. The degree of radial deformation may be quantified by a blow-up ratio or radial draw ratio:

$$\frac{\text{Inside Diameter of Deformed Tube}}{\text{Original Inside Diameter of Tube}}$$

In some embodiments, the radial draw ratio of a polymeric tube for use in fabricating a stent may be between about 1 and 20, or more narrowly between about 2 and 6. Similarly, the degree of axial deformation may be quantified by an axial draw ratio:

$$\frac{\text{Length of Deformed Tube}}{\text{Original Length of Tube}}$$

In some embodiments, a stent can be fabricated from the radially expanded tube by laser machining. The stent may then be crimped on to a delivery device such as a balloon. Therefore, the extruded tube must have a diameter that is less than a target diameter, the target diameter corresponding to a diameter at which a stent pattern is formed by laser machining or a diameter of a stent prior to crimping. Thus, the extruded tube can then be radially expanded to the target diameter.

The degree of induced strength due to radial expansion depends on the amount of radial expansion as quantified by the blow-up ratio. Thus, the degree of radial expansion is determined by the extruded diameter and the target diameter. In some embodiments, the extruded diameter can be used to determine the degree of radial expansion. The smaller the extruded diameter, the larger is the degree of radial expansion. In some embodiments, the extruded diameter can be controlled by the drawing of the polymer film as it exits the die. For a die having a diameter similar to the target diameter, the axial draw down ratio can be between 1 and 3. The axial drawdown ratio is defined as:

$$\frac{\text{Drawn Length of Tube}}{\text{Original Length of Tube}}$$

In further embodiments, it may be desirable to control the degree of crystallinity in a polymer tube during extrusion, radial deformation, and/or axial deformation to reduce or eliminate physical aging, creep, and stress relaxation in a stent. Additionally, it is also desirable to control crystallinity to increase the toughness of a stent.

As discussed above, physical aging, creep, and stress relaxation are due at least in part to rearrangement of polymer chains in amorphous regions of a polymer. Thus, as crystallinity increases in a polymer, physical aging, creep, and stress relaxation tend to reduce. Therefore, it is advantageous to use crystalline or semi-crystalline polymers for a stent to reduce or eliminate physical aging, creep, and stress relaxation.

However, crystalline and semi-crystalline polymers can be relatively brittle at biological conditions, i.e., the temperature of the human body. In particular, such polymers can have a Tg below the body temperature. These polymers can have a low fracture toughness and are thus susceptible to mechanical failure during use, for example, during crimping, deployment, and treatment. It is important for a stent to have a high fracture toughness throughout the range of stress experienced during use. For a semi-crystalline polymer, if the crystallinity is too high, example 50-60%, it is more likely that the polymer will be brittle under biological conditions.

Semi-crystalline polymers can contain both amorphous and crystalline domains at temperatures below their melting point. Amorphous regions are those in which polymer chains are in relatively disordered configurations. Crystalline domains are those in which polymer chains are in ordered configurations with segments of polymer chains essentially parallel to one another.

Figure 7:
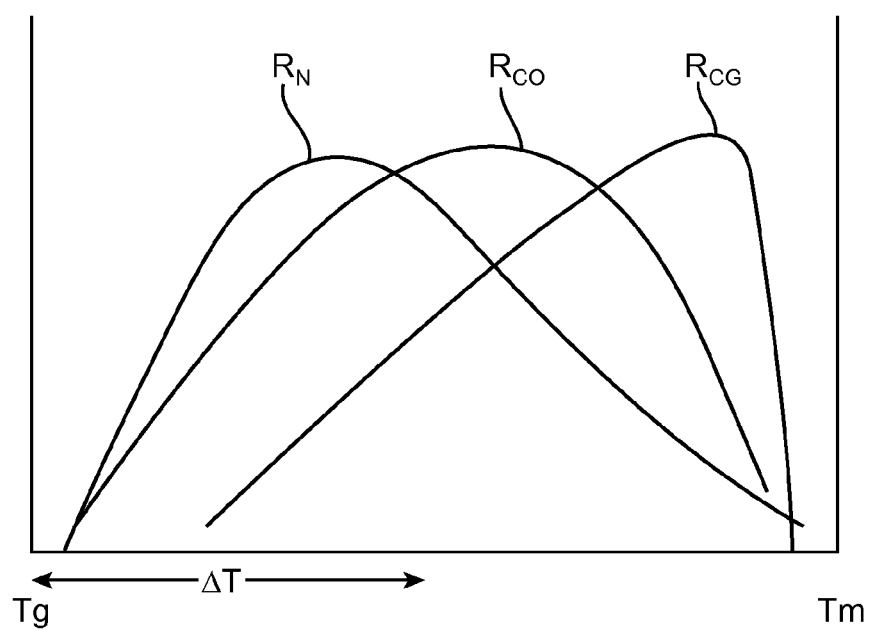
FIG. 7 depicts a schematic plot of the crystal nucleation rate and the crystal growth rate, and the overall rate of crystallization.

In certain embodiments, the crystallinity of an extruded tube, which is made from a polymeric material and a nucleating agent, can be controlled by controlling the temperature of cooling the annular film exiting the die. In general, crystallization tends to occur in a polymer at temperatures between Tg and Tm of the polymer. The rate of crystallization in this range varies with temperature. FIG. 7 depicts a schematic plot of the crystal nucleation rate ($R_N$), the crystal growth rate ($R_{CG}$), and the overall rate of crystallization ($R_{CO}$). The crystal nucleation rate is the growth rate of new crystals and the crystal growth rate is the rate of growth of formed crystals. The overall rate of crystallization is the sum of curves $R_N$ and $R_{CG}$.

In certain embodiments, the temperature of the annular tube exiting the extruder during cooling can be at a temperature in a range in which the crystal nucleation rate is larger than the crystal growth rate. In one embodiment, the temperature can be in a range in which the crystal nucleation rate is substantially larger than the crystal growth rate. For example, the temperature can be where the ratio of the crystal nucleation rate to crystal growth rate is 2, 5, 10, or greater than 10. In another embodiment, the temperature range may be in range, ΔT shown in FIG. 7, between about Tg to about 0.5 (Tm−Tg)+Tg.

Additionally, crystallinity in a polymeric tube can also be controlled during radial deformation to increase fracture toughness and reduce physical aging, creep, and stress relaxation. As indicated above, it is desirable to radially deform at a temperature above a Tg of the polymer to facilitate deformation and to heat set the polymer above the Tg. As a result, crystallization tends to occur in the polymer during deformation and heat setting. In addition, crystallinity in addition to orientation may be induced in the polymer during deformation. This process is referred to as strain-induced crystallization.

Thus, embodiments of the method can include radially deforming and/or heat setting in temperature ranges described above for extrusion. Deforming and heat setting a tube in such a temperature range can result in a radially deformed tube with a higher fracture toughness and reduced physical aging, creep, and stress relaxation for the same reasons as explained above for extrusion.

In other embodiments, an extruded tube can be formed that is amorphous or substantially amorphous. An amorphous polymeric tube can be formed by quickly quenching the annular tube exiting the die so that its temperature is reduced to a temperature from above Tm to below Tg so that very little or substantially no crystallization occurs in the polymer during cooling. Thus, an amorphous glassy polymer can be formed. Then, to increase the crystallization, the tube can then be deformed and heat set, as described above, at a temperature that results in high fracture toughness and with reduced physical aging, creep, and stress relaxation.

Polymers can be biostable, bioabsorbable, biodegradable or bioerodable. Biostable refers to polymers that are not biodegradable. The terms biodegradable, bioabsorbable, and bioerodable are used interchangeably and refer to polymers that are capable of being completely degraded and/or eroded when exposed to bodily fluids such as blood and can be gradually resorbed, absorbed, and/or eliminated by the body. The processes of breaking down and eventual absorption and elimination of the polymer can be caused by, for example, hydrolysis, metabolic processes, bulk or surface erosion, and the like.

It is understood that after the process of degradation, erosion, absorption, and/or resorption has been completed, no part of the stent will remain or in the case of coating applications on a biostable scaffolding, no polymer will remain on the device. In some embodiments, very negligible traces or residue may be left behind. For stents made from a biodegradable polymer, the stent is intended to remain in the body for a duration of time until its intended function of, for example, maintaining vascular patency and/or drug delivery is accomplished.

Representative examples of polymers that may be used to fabricate or coat an implantable medical device include, but are not limited to, poly(N-acetylglucosamine) (Chitin), Chitosan, poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(D,L-lactide), poly(caprolactone), poly(lactide-co-caprolactone), poly(trimethylene carbonate), poly(lactide-co-trimethylene carbonate), polyester amide, poly(glycolic acid-co-trimethylene carbonate), poly(lactide-co-p-dioxanone), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Another type of polymer based on poly(lactic acid) that can be used includes graft copolymers, and block copolymers, such as AB block-copolymers ("diblock-copolymers") or ABA block-copolymers ("triblock-copolymers"), or mixtures thereof.

Additional representative examples of polymers that may be especially well suited for use in fabricating or coating an implantable medical device include ethylene vinyl alcohol copolymer (commonly known by the generic name EVOH or by the trade name EVAL), poly(butyl methacrylate), poly (vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

The embodiments which include a nucleating agent can be used with any of these aforementioned polymers.

EXAMPLES

The examples and experimental data set forth below are for illustrative purposes only and are in no way meant to limit the invention. The following examples are given to aid in understanding the invention, but it is to be understood that the invention is not limited to the particular materials or procedures of examples.

Example 1

PLGA Stent Preparation Using PGA as a Nucleating Agent

1. Blend Preparation—1 kg of high molecular weight PLGA (LLA:GA=90:10) is blended with 50 g PGA at room temperature in a mechanical blender, or through melt blending using a twin screw extruder, or through solution blending by dissolving both PLGA and PGA in a co-solvent and precipitating them in a non-solvent.
2. Tubing Extrusion—The PLGA tubing is formed through extrusion in a single or twin screw extruder with a puller. The size of the extruded tubing is set at 0.02" for the ID and 0.07" for the OD. The tubing is cooled to room temperature.
3. Stent Preparation—In order to further increase the crystallinity of the extruded PLGA tubing, the tubing with ID=0.02" and OD=0.07" is expanded in a glass mold at about 180° F. The tubing is then cooled to room temperature. The expanded tubing has an ID=0.12" and an OD=0.13" and is cut by a laser and crimped to a smaller size of 0.05".

Example 2

PLGA Stent Preparation Using PGLA as a Nucleating Agent

1. Blend Preparation—1 kg of high molecular weight PLGA (LLA:GA=90:10) is blended with 50 g PGLA (GA:LLA=98:2) at room temperature in a mechanical blender, or through melt blending using a twin screw extruder, or through solution blending by dissolving both PLGA and PGLA in a co-solvent and precipitating them in a non-solvent.
2. Tubing Extrusion—The PLGA tubing is formed through extrusion in a single or twin screw extruder with a puller. The size of the extruded tubing is set at 0.02" for the ID and 0.07" for the OD. The tubing is cooled to room temperature.
3. Stent Preparation—In order to further increase the crystallinity of the extruded PLGA tubing, the tubing with ID=0.02" and OD=0.07" is expanded in a glass mold at about 180° F. The tubing is then cooled to room temperature. The expanded tubing has an ID=0.12" and an OD=0.13" and is cut by a laser and crimped to a smaller size of 0.05".

Example 3

PLGA Stent Preparation Using Nano Magnesium Silicate Hydrate as a Nucleating Agent 1. Blend Preparation—1 kg of high molecular weight PLGA (LLA:GA=90:10) is blended with 10 g nano magnesium silicate hydrate at room temperature in a mechanical blender, or through melt blending using a twin screw extruder, or through solution blending by dissolving PLGA in a solvent with suspended nano magnesium silicate hydrate particles and precipitating the mixture in a non-solvent.
2. Tubing Extrusion—The PLGA tubing is formed through extrusion in a single or twin screw extruder. The size of the extruded tubing is set at 0.02" for the ID and 0.07" for the OD. The tubing is cooled to room temperature.
3. Stent Preparation—In order to further increase the crystallinity of the extruded PLGA tubing, the tubing with ID=0.02" and OD=0.07" is expanded in a glass mold at about 180° F. The tubing is then cooled to room temperature. The expanded tubing has an ID=0.12" and an OD=0.13" and is cut by a laser and crimped to a smaller size of 0.05".

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method for fabricating a polymeric stent comprising:
   combining a main polymer with a nucleating agent to form a polymer mixture,
   wherein the main polymer is poly(lactide-co-glycolide) (PLGA) with an L-lactide:glycolide ratio of 85:15 to 95:5,
   wherein the nucleating agent is poly(glycolide-co-lactide) with less than 10 wt % L-lactide,
   wherein the nucleating agent has a faster crystallization rate than the main polymer and a faster degradation rate than polyglycolide,
   wherein the nucleating agent is present in the range of 0.1 to 10% by weight of the polymer mixture;
   forming polymer tubing from the polymer mixture, wherein the nucleating agent increases crystallinity of the tubing; and
   fabricating the stent from the tubing.

2. The method of claim 1, further comprising a stress inducing crystallization step, wherein the nucleating agent enhances the crystallization during the stress induced crystallization step.

3. The method of claim 2, wherein the stress inducing crystallization step also decreases crystal size.

4. The method of claim 2, wherein the stress inducing crystallization step includes deformation of the polymer tubing radially, axially, or both before fabricating the stent from the deformed tubing.

5. The method of claim 2, wherein the stress inducing crystallization step is carried out before fabricating the stent by radially deforming the formed polymer tubing for fabricating a stent from the deformed polymer tubing, wherein heating of the polymer tubing and increasing an internal tubing pressure higher than ambient facilitates the radial deforming.

6. The method of claim 2, wherein the stress inducing crystallization step includes axial deformation using blow molding and by applying a tensile force by a tension source to at least one end of the polymer tubing.

7. The method of claim 6, wherein the stress inducing crystallization step comprises applying a tensile force at both ends of the polymer tubing.

8. The method of claim 2, wherein the stress inducing crystallization step comprises heat setting the polymer tubing at a temperature above Tg.

9. The method of claim 1, wherein the nucleating agent is present in the range of 0.2 to 5% by weight of the polymer mixture.

10. The method of claim 1, wherein the main polymer and the nucleating agent are combined by solution blending, the solution blending comprising dissolving the PLGA and the nucleating agent in a co-solvent and precipitating the PLGA and nucleating agent to form the mixture.

* * * * *

UNITED STATES PATENT AND TRADEMARK OFFICE
CERTIFICATE OF CORRECTION

PATENT NO. : 8,252,215 B2  
APPLICATION NO. : 12/059423  
DATED : August 28, 2012  
INVENTOR(S) : Wang Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 979 days.

Signed and Sealed this  
Seventeenth Day of March, 2020

Andrei Iancu  
*Director of the United States Patent and Trademark Office*